United States Patent [19]

Bournay, Jr. et al.

[11] Patent Number: 4,545,381

[45] Date of Patent: Oct. 8, 1985

[54] ADAPTER FOR CONVERTING A METAL ENCAPSULATED IMPLANTABLE CARDIAC PACER TO AN EXTERNALLY WORN CARDIAC PACER

[75] Inventors: Frederick M. Bournay, Jr., Evansville, Ind.; Joel F. Giurtino, Miami, Fla.

[73] Assignee: Cordis Corporation, Miami, Fla.

[21] Appl. No.: 656,696

[22] Filed: Oct. 1, 1984

[51] Int. Cl.⁴ ............................................. A61N 1/00
[52] U.S. Cl. .............................................. 128/419 P
[58] Field of Search .......... 128/419 P, 419 PS, 419 R

[56] References Cited

U.S. PATENT DOCUMENTS

| | | | |
|---|---|---|---|
| 4,243,042 | 1/1981 | Ware | 128/419 P |
| 4,248,237 | 2/1981 | Kenny | 128/419 P |
| 4,314,562 | 2/1982 | Ware | 128/419 P |
| 4,347,849 | 9/1982 | Congdon | 128/419 P |
| 4,423,732 | 1/1984 | Tarjan et al. | 128/419 P |

Primary Examiner—William E. Kamm
Attorney, Agent, or Firm—Henry W. Collins; Thomas R. Vigil

[57] ABSTRACT

The adapter is adapted to convert a metal encapsulated device, such as an implantable cardiac pacer to an externally worn cardiac pacer whereby a physician can try various pacers before selecting an appropriate implantable cardiac pacer to meet the pacing needs of a patient and before implantation of any cardiac pacer. The adapter comprises a housing and a mechanism within the housing which is in direct electrical contact with the pacer and which secures the pacer within the housing in an electrically conductive manner. The adapter further comprises an interfacing mechanism for securing a conductive lead assembly to the housing in an electrically conductive manner and for electrically connecting the lead assembly to the pacer within the housing in an electrically conductive manner.

22 Claims, 8 Drawing Figures

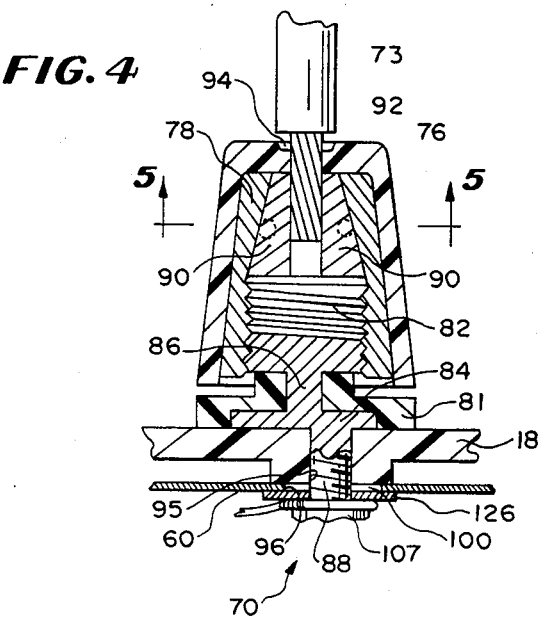
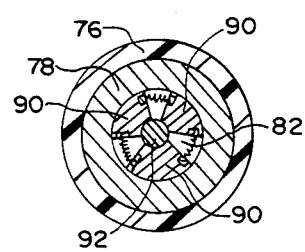
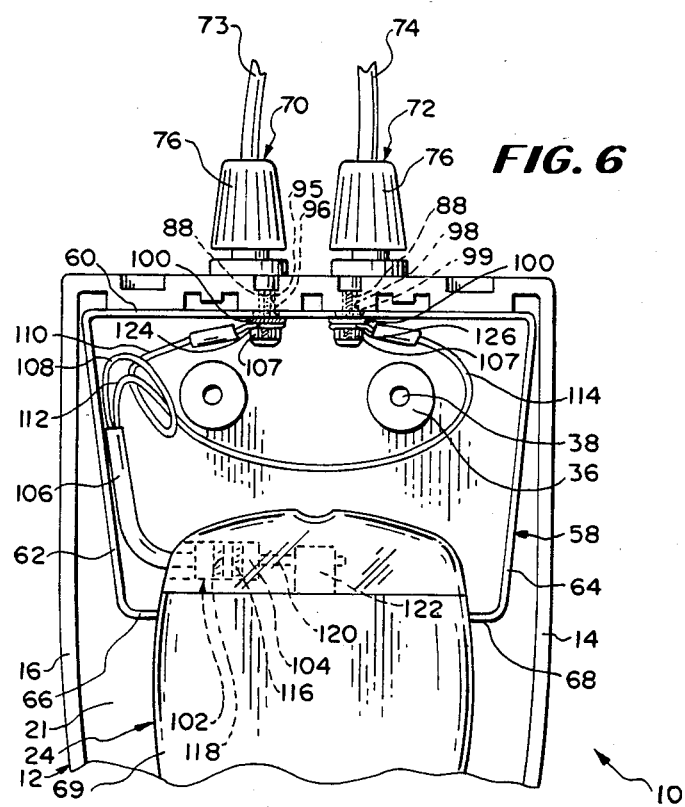

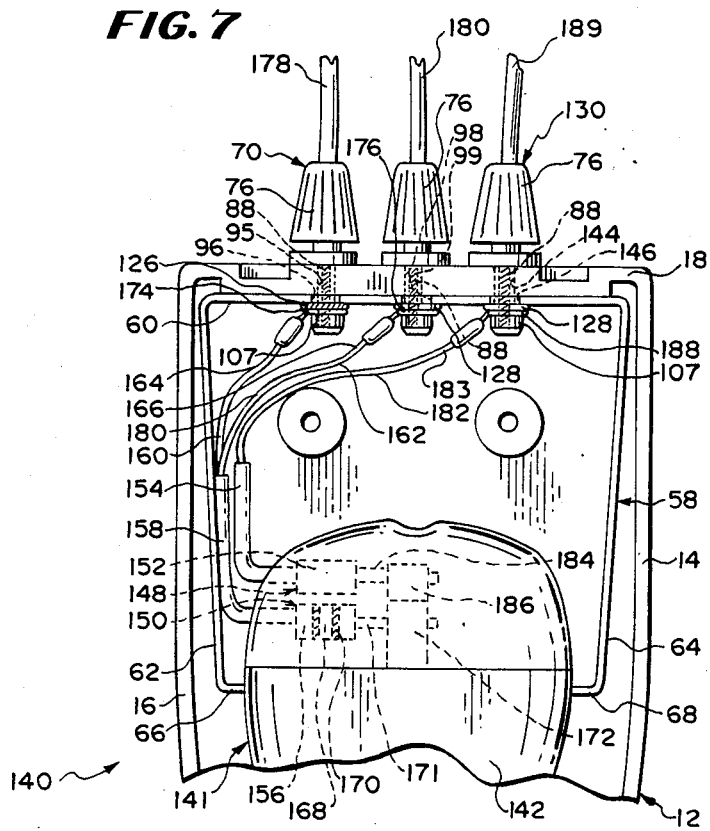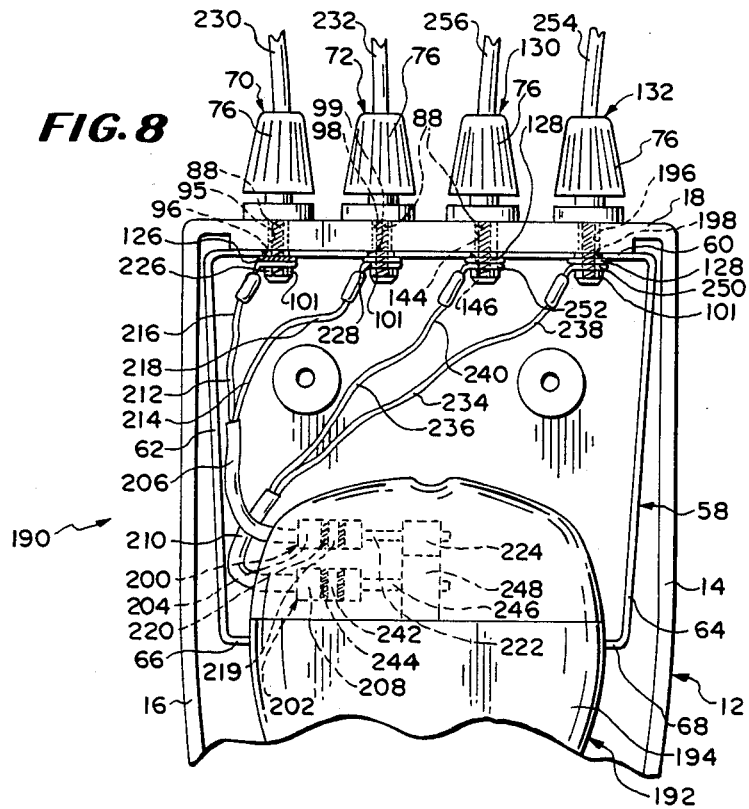

ADAPTER FOR CONVERTING A METAL ENCAPSULATED IMPLANTABLE CARDIAC PACER TO AN EXTERNALLY WORN CARDIAC PACER

BACKGROUND OF THE INVENTION

1. Field of the Invention

The present invention relates to an adapter by which a metal encapsulated implantable cardiac pacer can be converted to an externally worn cardiac pacer. The adapter includes a housing within which an implantable cardiac pacer can be secured by an electrically conductive spring-clip member. The housing includes a plurality of conductive chuck assemblies for electrically connecting a temporary pervenous lead assembly to the cardiac pacer secured within the housing. With this adapter, a physician can try various cardiac pacers before selecting the most appropriate implantable cardiac pacer model to meet the cardiac pacing needs of a patient and before the implantation of any particular cardiac pacer.

2. Description of the Prior Art

Heretofore various enclosure systems and connector systems for implantable cardiac pacers have been proposed. Examples of such previously proposed enclosure systems and connector systems are disclosed in the following U.S. patents:

| U.S. Pat. No. | PATENTEE |
|---|---|
| 4,243,042 | Ware |
| 4,248,237 | Kenny |
| 4,314,562 | Ware |
| 4,347,849 | Congdon |
| 4,423,732 | Tarjan et al. |

The Ware U.S. Pat. Nos. 4,243,042 and 4,314,562 disclose an enclosure system for a body implantable electrical stimulator which includes a stimulator enclosure which is formed of first and second preformed members having a generally circular configuration. A cup is also provided into which the components of a body implantable electrical stimulator may be assembled, the cup being configured to fit within the preformed electrical stimulator enclosure. The components of the electrical stimulator are secured within the cup by an encapsulating material which substantially fills the cup, or by elements which engage one or more components to mechanically maintain them in position.

The Kenny U.S. Pat. No. 4,248,237 discloses a case for implantation into a human or animal body comprising two molded plastic chamber members which mate to define a complete chamber. One of the plastic chamber members includes a socket member which is connected to an electronic system. The electronic system comprises a pacemaker and a battery which are housed within the complete chamber.

The Congdon U.S. Pat. No. 4,347,849 discloses a connector system which is used with an external cardiac pacer and which provides an electrical connection to an associated pacer lead assembly. The system includes a pair of terminal blocks each having a bore for receiving a respective connector pin of the lead assembly. A pair of locking plates are pivotally mounted in wedge shaped recesses in the connector blocks. Each plate has an aperture through which the connector plates extend. The locking plates are spring biased into engagement with the connector pins to prevent inadvertent removal of the pins from the bores. An operator actuated release button can be operated to pivot the locking plates from engagement with the pins to enable the pins to be removed from the pacer.

The Tarjan et al. U.S. Pat. No. 4,423,732 discloses a sterile connector system for a packaged pacer that permits testing and use of a pacer while it remains sealed in a sterile container.

As will be described in greater detail hereinafter, the adapter of the present invention differs from the various enclosure systems and connector systems for implantable cardiac pacers previously proposed by providing a housing having an electrically conductive spring-clip member within the housing which acts as an anode connector and which secures an implantable cardiac pacer within the housing in an electrically conductive manner. The housing has two or more conductive chuck assemblies mounted thereon for establishing an electrical connection of the electrical conductors of a temporary pervenous lead assembly to a pacer within the housing. By providing a housing within which a pacer can be secured and to which a temporary pervenous lead assembly can be connected, a physician can try a number of pacers before selecting an appropriate implantable cardiac pacer model to meet the pacing needs of a patient and before implantation of the appropriate cardiac pacer.

SUMMARY OF THE INVENTION

According to the invention, there is provided an adapter for converting a metal encapsulated, implantable device, such as a cardiac pacer, to an externally worn device. The adapter comprises a housing and a mechanism for securing the device within the housing, the mechanism for securing the pacer within the housing being in electrical contact with a metal housing of the device. The adapter further comprises an interfacing assembly for securing a conductive lead assembly to the device within the housing in an electrically conductive manner.

BRIEF DESCRIPTION OF THE DRAWINGS

FIG. 4 is a sectional side view of a chuck assembly mounted on the adapter housing for securing a temporary pervenous lead assembly to the adapter in an electrically conductive manner.

FIG. 5 is a cross-sectional view of the chuck assembly shown in FIG. 4 and is taken along line 5—5 of FIG. 4.

FIG. 6 is a rear view of the adapter shown in FIGS. 1-3.

FIG. 7 is a rear view of another embodiment of the adapter similar to the adapter shown in FIG. 1.

FIG. 8 is a rear view of still another embodiment of the adapter similar to the adapter shown in FIG. 1.

DESCRIPTION OF THE PREFERRED EMBODIMENT

Figure 1:
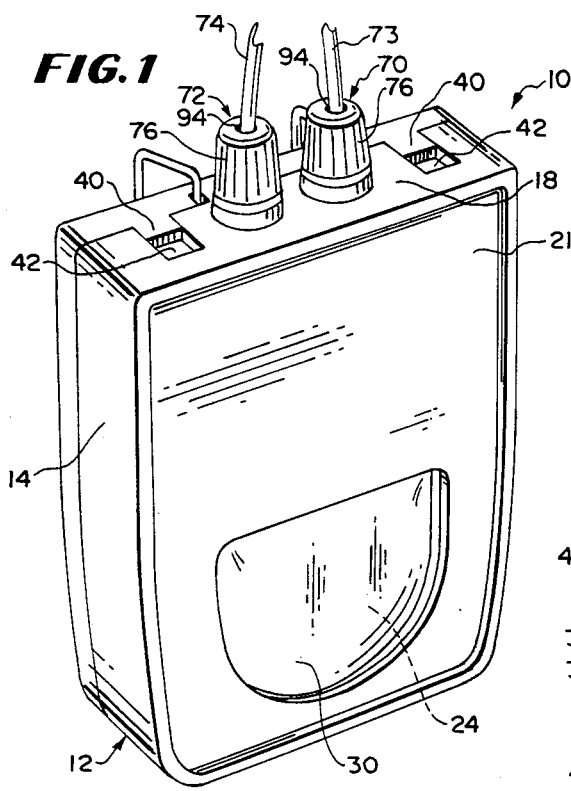
FIG. 1 is a front perspective view of an adapter for converting an implantable cardiac pacer to an externally worn cardiac pacer constructed in accordance with the teachings of the present invention.
Figure 2:
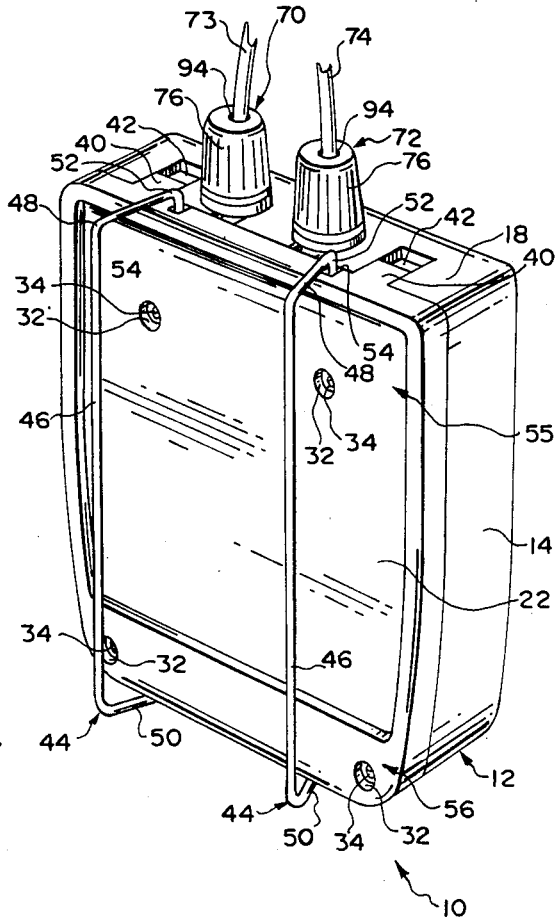
FIG. 2 is a rear perspective view of the adapter shown in FIG. 1.
Figure 3:
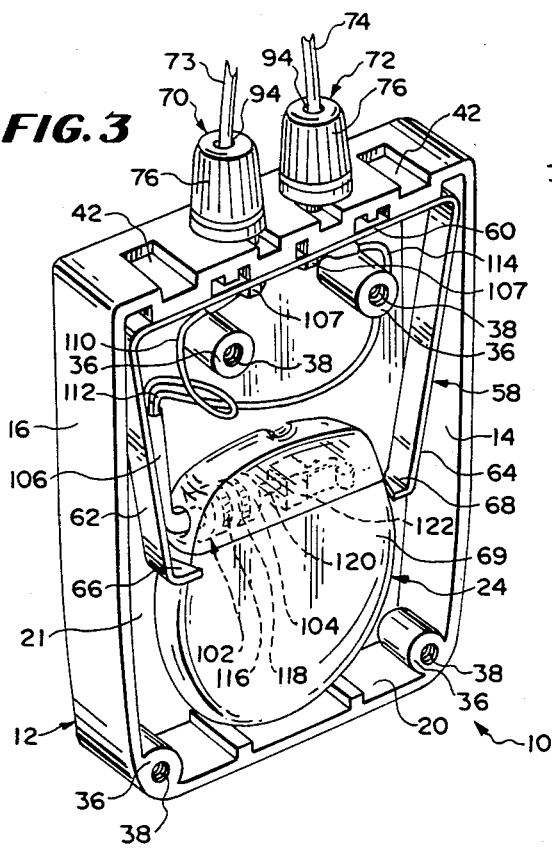
FIG. 3 is a rear perspective view of the adapter shown in FIG. 2 with a removable rear wall removed from a housing of the adapter.

Referring to FIGS. 1–3, there is illustrated therein an adapter 10 for converting an implantable cardiac pacer to an externally worn cardiac pacer. The implantable cardiac pacer is housed within the adapter 10 which is constructed according to the teachings of the present invention.

The adapter 10 comprises a housing 12 made of a nonconductive thermoplastic material such as polycarbonate, or acrylonitrile butadiene styrene (ABS), and includes two side walls 14, 16, upper and lower end walls 18, 20, a front wall 21 and a removable rear wall 22. The two side walls 14, 16, the upper and lower end walls 18, 20, and the front and rear walls 21, 22 define an open area 23 (FIG. 3) having dimensions sufficient to contain a cardiac pacer 24 therein.

The side walls 14, 16 and the upper and lower end walls 18, 20 are formed from a single piece of polycarbonate, or ABS, and the front wall 21 is also made of polycarbonate or ABS and is glued or otherwise permanently fixed to the side walls 14, 16 and the upper and lower end walls 18, 20 and includes a transparent window 30 made of a suitable transparent thermoplastic material, such as Mylar. The window 30 permits an observer, such as a physician, to view the caradiac pacer 24 (shown in phantom in FIG. 1) which is housed within the housing 12 in order to ascertain the type or model of a cardiac pacer secured within the housing 12 and to ascertain the serial number of a pacer secured within the housing 12.

The removable rear wall 22 (FIG. 2) is provided with four holes 32 through which four screws 34 are received. Four posts 36 (FIG. 3) are situated within the housing 12 and are upstanding from and perpendicular to the front wall 21. The posts 36 include threaded bores 38 which are threadably engageable with the screws 34 so that the rear wall 22 can be removed and/or replaced for placement and/or removal of the cardiac pacer 24.

The removable rear wall 22 is further provided with two rectangular-in-cross-section guide posts 40 which are matingly received into two elongate guide channels 42 which are formed into the upper end wall 18 of the housing 12 in order to accurately align and hold in place the rear wall 22 which is secured to the housing 12 by the four screws 34.

The adapter 10 is provided with two removable wire bales or brackets 44 through which a belt-like fastener (not shown) can be received so that the adapter 10 can be fastened to and externally worn by a patient around, for example, the waist of the patient. The bales 44 have a U-shaped configuration and comprise a base portion 46 and upper and lower arm portions 48, 50 which are perpendicular to the base portion 46. The upper and lower arm portions 48, 50 include inwardly projecting end portions 52 which are parallel to the base portion 46 and which are received into four recesses 54 molded into the upper and lower ends 55, 56 of the rear wall 22. In this manner, the wire bales 44 are rotatably held in position between the rear wall 22 and the upper and lower end walls 18, 20 and are permitted to rotate about approximately a 180 degree axis relative to the rear wall 22.

Since the wire bales 44 are removable upon removal of the rear wall 22, the wire bales 44 can be removed and the adapter 10 can be carried in either, for example, a shirt pocket, pants pocket, or a pouch worn by a patient, instead of securing the adapter 10 to the patient with a belt-like fastener.

Referring now to FIGS. 3 and 6, there is illustrated therein the adapter 10 with the cardiac pacer 24 secured within the housing 12 by a spring-clip or contact member 58. The spring-clip 58 is formed from an elongated strip of electrically conductive material, such as stainless steel, and includes a base 60 and first and second arms 62, 64 which are biased inwardly at approximately an 80 degree angle relative to the base 60 of the spring-clip 58. The distal ends 66, 68 of the first and second arms 62, 64 are bent and turned inwardly and are urged relative to each other in a spring-like manner. The cardiac pacer 24 is releasably secured and held between the distal ends 66, 68 of the arms 62, 64 with the distal ends 66, 68 of the arms 62, 64 mechanically and electrically in contact with a metallic pacer case 69 of the pacer 24.

In the preferred embodiment of the present invention (FIGS. 1–3), the housing 12 of the adapter 10 further includes first and second conductive chuck assemblies 70, 72 which are secured to and extend above the upper end wall 18 of the housing 12. The chuck assemblies 70, 72 each are adapted to receive an anode conductor 73 and a cathode conductor 74 of a temporary pervenous pacing lead assembly for electrically coupling same to the cardiac pacer 24 secured within the housing 12, as will be described in greater detail hereinafter.

As further illustrated in FIGS. 4 and 5, each chuck assembly 70, 72 includes a cap member 76 made of a nonconductive material, such as polycarbonate or ABS, and includes an internally threaded conductive sleeve member 78 disposed within the cap member 76 and having a conical configuration. Each chuck assembly 70, 72 further includes a base member 80 made of an electrically conductive material surrounded by a nonconductive sleeve 81 and comprising an externally threaded chuck seat 82 which is threadably engagable with the sleeve member 78, and a base 84 joined to the chuck seat 82 by a shaft 86.

As will be described in greater detail hereinafter, the base 84 is provided with a threaded post 88 which secures each chuck assembly 70, 72 to the upper end wall 18 of the housing 12, and which also serves to electrically connect an electrical conductor of a temporary pervenous lead assembly to the pacer 24 secured within the housing 12.

Each chuck assembly 70, 72 is generally conical and includes three chucks 90 which are freely positioned within the sleeve member 78 of the cap member 76 and which movably rest upon the chuck seat 82. Since the chucks 90 and the sleeve member 78 are in a conforming, conical configuration, when the cap member 76 is rotated in a clockwise direction from an uppermost or open-chuck position to a lowermost or close-chuck position (FIG. 4), the cap member 76 moves in a downward direction and urges the sleeve member 78 against the chucks 90 which rest on the chuck seat 82.

An uninsulated distal end 92 of the anode conductor 73 of the temporary pervenous lead assembly (not shown) is inserted into a distal opening 94 in the cap member 76 of the chuck assembly 70, and between the chucks 90 when they are in an open position. The cap member 76 is then rotated in a clockwise direction, and moves in a downward direction causing the chucks 90 to bear against the distal end 92 of the anode conductor 73 therebetween and makes a good electrical and mechanical connection with the anode conductor 73. The cathode conductor 74 is electrically and mechanically fixed in the chuck assembly 72 in a similar manner.

In this embodiment, the threaded post 88 of the first chuck assembly 70 extends into and within the housing 12 through a hole 95 in the upper end wall 18 and through a hole 96 in the base 60 of the spring-clip 58. Similarly, the threaded post 88 of the second chuck assembly 72 extends into and within the housing 12 through a hole 98 in the upper end wall 18 and through a hole 99 in the base 60 of the spring-clip 58.

Referring again to FIG. 4, it is to be appreciated that according to the teachings of the present invention, the holes 96, 99 in the base 60 of the spring-clip 58 are of a diameter substantially larger than the diameter of the threaded posts 88 of the chuck assemblies 70, 72, thereby providing an insulating space or gap 100 between the threaded posts 88 and the spring-clip 58. In this manner, and as will be described in greater detail hereinafter, the threaded posts 88 are isolated from and thereby not in electrical contact with the base member 60 of the spring-clip 58.

Referring now to FIG. 6, the cardiac pacer 24 is a ventricular cardiac pacer and the metallic pacer case 69 is made of a material such as titanium which serves as the anode of the pacer 24 and is in direct electrical contact with the distal ends 66, 68 of the arms 62, 64 of the spring-clip 58. The pacer 24 is provided with a socket 102 for receiving a plug 104 (shown in phantom) of a plug assembly 106.

A nut 107 is threadably engagable on each post 88 and when rotated in a clockwise direction, moves in an upward direction to thereby secure each chuck assembly 70, 72 to the upper end wall 18 of the housing 12 and with the spring-clip 58 secured between the upper end wall 18 and the nut 107.

The plug assembly 106 includes a first jumper conductor 108 having a distal end 110 and a proximal end (not shown), and a second jumper conductor 112 having a distal end 114 and a proximal end (not shown). The proximal end of the conductor 108 is electrically connected to an anode ring 116 of the plug 104 and is in direct electrical contact with an anode connector 118 in the socket 102 to provide electrical connections from the lead conductors 73 and 74 to the pacer 24.

The distal end 110 of the conductor 108 has an electrically conductive eyelet 124 which is positioned on and is in direct electrical contact with the post 88 of the chuck assembly 70 and secured thereon in an electrically conductive manner between the base 60 and the nut 101 with an electrically conductive metallic washer 126 interposed between the base 60 and the eyelet 124. Since the eyelet 124 is in direct electrical contact with the base 60 of the spring-clip member 58 through the washer 126, the anode conductor 73 of the temporary pervenous lead assembly, which is secured to the chuck assembly 70 as heretofore described, is electrically connected to the pacer 24 through the conductor 108 and the spring-clip 58 to thereby provide a first anode connection to the pacer 24 through the distal ends 66, 68 of the spring-clip 58 which are in direct mechanical and electrical contact with the metallic body 69 of the pacer 24 and a second anode connection through the conductor 108 of the plug assembly 106.

Similarly, the distal end 114 of the conductor 112 has an electrically conductive eyelet 126 which is positioned on and in direct electrical contact with the post 88 of the chuck assembly 72 and secured thereon with a nonconductive, insulative washer 128 interposed between the base 60 and another nut 107. The insulative washer 128 insulates the eyelet 126 from the spring-clip 58 so that the cathode conductor 74 of the temporary pervenous lead assembly is electrically connected only to the eyelet 126 and to the cathode of the pacer 24 through the conductor 114. It is to be appreciated that since the hole 99 of the base 60 through which the post 88 of the chuck assembly 72 extends is larger in diameter than the diameter of the post 88, the post 88 is not in direct electrical contact with the base 60, and the eyelet 126 is insulated from the base 60 by the insulative washer 128, so that the cathode connection does not short-out the pacer 24.

It is to be appreciated that, according to the teachings of the present invention, the adapter 10 can be modified to accommodate various types and models of pacers which are adapted for various modes of cardiac pacing, such as atrial-ventricular pacing, as well as being adapted to accommodate various pacing leads which are electrically connected to the adapter 10, such as unipolar and/or bipolar pacing leads.

For example, the adapter can be modified, depending upon the pacing mode preferred, to include a third conductive chuck assembly 130 in addition to the first and second chuck assemblies 70, 72 as shown in FIG. 7 for unipolar or bipolar dual-chamber atrial-ventricular pacing.

In still another embodiment shown in FIG. 8, the adapter can be modified to include a fourth conductive chuck assembly 132 in addition to the chuck assemblies 70, 72 and 130 wherein two of the chuck assemblies serve as the anode and cathode connectors for an atrial temporary pervenous lead assembly and two of the chuck assemblies serve as the anode and cathode connectors for a ventricular temporary pervenous lead assembly in order to accommodate bipolar pacing lead assemblies for connection to a dual-chamber, atrial-ventricular cardiac pacer.

In the following description of the modified embodiments shown in FIGS. 7 and 8, parts identical to parts of the adapter 10 are identified with the same reference numerals.

Referring now to FIG. 7, there is illustrated therein a modified adapter 140 and a dual-chamber atrial-ventricular cardiac pacer 141 having a metal casing 142 secured within the housing 12 by the spring-clip 58 which is in direct electrical contact with the metal casing 142 of the pacer 141. In this embodiment, the housing 12 of the adapter 141 further includes the third electrically conductive chuck assembly 130. The chuck assembly 130 includes a threaded post 88 which extends into and within the housing 12 through a hole 144 provided in the upper end wall 18 and through a hole 146 in the base 60 of the spring-clip 58, respectively. The spring-clip 58 is secured between the upper end wall and nut 107 threadably received on the parts 88.

The metal casing 142 of the atrial-ventricular pacer 141 is also made of a material such as titanium which serves as an anode terminal of the pacer 141 and is in direct electrical contact with the distal ends 66, 68 of the arms 62, 64 of the spring-clip 58.

The cardiac pacer 141 of the type shown in FIG. 7 includes a plug receiving socket 148 (shown in phantom) and a plug receiving socket 150 (shown in phantom) which are adapted to receive a plug 152 (shown in phantom) of a plug assembly 154 and a plug 156 (shown in phantom) of a plug assembly 158, respectively.

The plug assembly 158 includes a jumper conductor 160 and a jumper conductor 162 having distal ends 164, 166, respectively, and proximal ends (not shown) which are electrically connected to the plug 156. The proximal end of the conductor 160 is electrically connected to an anode ring 168 of the plug 156 which is in direct electrical contact with an anode sleeve 170 in the plug assembly receiving socket 150 in order to provide an anode connection for a ventricular temporary pervenous lead assembly (comprising lead conductors 178 and 180) to the pacer 141.

Similarly, the proximal end of the conductor 162 is electrically connected to a cathode pin 171 of the plug 156 and is in direct electrical contact with a cathode connector socket 172 of the plug assembly receiving socket 150 in order to provide a cathode connection for the ventricular temporary pervenous lead assembly to the pacer 140.

The distal ends 164, 166 of the anode and cathode conductors 160, 162, respectively, include electrically conductive eyelets 174, 176 thereon. The eyelet 174 of the anode conductor 160 is positioned on and in direct electrical contact with the post 88 of the chuck assembly 70 and secured thereon in an electrically conductive manner between the base 60 and a metallic washer 126 and a nut 107. Since the eyelet 174 is in direct electrical contact with the spring-clip 58 through the washer 126, the anode conductor 178 of the ventricular temporary pervenous lead assembly (not shown) secured to the chuck assembly 70 is electrically connected to the pacer 141 through the anode conductor 160 which provides for a first anode connection to the pacer 141, and is electrically connected to the pacer 141 through the spring-clip 58 to thereby provide for a second anode connection to the pacer 141 for the ventricular temporary pervenous lead assembly.

The eyelet 176 on the conductor 162 is positioned on and is in direct electrical contact with the post 88 of the chuck assembly 72 and secured thereon by a nut 107 and insulated from the base 60 by a nonconductive, insulative washer 128 interposed between the base 60 and the eyelet 176. The insulative washer 128 insulates the eyelet 176 of the cathode conductor 162 from the spring-clip 58 so that cathode conductor 180 of the ventricular temporary pervenous lead assembly is electrically connected to the eyelet 126 and to the cathode of the pacer 141 through the cathode conductor 162 and insulated from the spring-clip 58 by the insulative washer 128 to thereby provide a cathode connection for the ventricular temporary pervenous lead assembly to the pacer 140 without shorting out the electrical system of the pacer 141.

The plug assembly 154 includes a conductor 182 having a distal end 183 and a proximal end (not shown) electrically connected to the plug 152. The proximal end of the conductor 182 is electrically connected to a cathode pin 184 of the plug 152 and is in direct electrical contact with a cathode connector socket 186 of the plug assembly receiving socket 148 in order to provide a cathode connection for an atrial temporary pervenous lead assembly with remote anode connected to the chuck assembly 72 and to the pacer 141.

The distal end 183 of the cathode conductor 182 has an electrically conductive eyelet 188 which is positioned on and is in direct electrical contact with the post 88 of the chuck assembly 130 and secured thereon in an electrically conductive manner by a nut 107 with a nonconductive, insulative washer 128 interposed between the base 60 and the eyelet 188. Since the eyelet 188 is insulated from the spring-clip 58 by the washer 128 and is in electrical contact with the post 88 of the chuck assembly 130, cathode conductor 189 of the atrial temporary pervenous lead assembly with remote anode (not shown), which is secured to the chuck assembly 72 in an electrically conductive manner, is electrically connected to the eyelet 188 and to the cathode of the pacer 141 through the conductor 182 and insulated from the spring-clip 58 by the insulative washer 128 thereby to provide a cathode connection for the atrial temporary pervenous lead assembly with remote anode to the pacer 141 without shorting out the electrical system of the pacer 141. The anode of the other lead assembly connected to anode conductor 178 provides a remote anode for the lead assembly including cathode conductor 189.

Refering now to FIG. 8, there is illustrated therein a modified adapter 190 and a dual-chamber, atrial-ventricular cardiac pacer 192 having a metal casing 194 secured within the housing 12 by the spring-clip 58. In this embodiment, the housing 12 includes a fourth conductive chuck assembly 132 which includes a threaded post 88 which extends into and within the housing 12 through a hole 196 in the upper end wall 18 and through a hole 198 in the base 60 of the spring-clip 58, respectively, and secured thereon by a nut 107.

The metal casing 194 of the pacer 192 is also made of a metal such as titanium which serves as the anode of the pacer 192 and is in direct electrical contact with the distal ends 66, 68 of the arms 62, 64 of the spring-clip 58.

The cardiac pacer 192 of the type shown in FIG. 8 includes a plug assembly receiving socket 200 (shown in phantom) and a plug assembly receiving socket 202 (shown in phantom) which are adapted to receive plug 204 (shown in phantom) of a plug assembly 206 and a plug 208 (shown in phantom) of a plug assembly 210, respectively.

The plug assembly 206 includes an anode jumper conductor 212 and a cathode jumper conductor 214 having distal ends 216, 218, respectively, and proximal ends (not shown) electrically connected to the terminal plug 204. The proximal end of the conductor 212 is electrically connected to an anode ring 219 of the plug 204 which is in direct electrical contact with an anode sleeve 220 in the plug receiving socket 200 in order to provide an anode connection of the conductor 230 to the pacer 192.

The proximal end of the conductor 214 is electrically connected to a cathode pin 222 of the plug 204 and is in direct electrical contact with a cathode connector socket 224 of the plug receiving socket 200 in order to provide a cathode connection for the atrial temporary pervenous lead assembly to the pacer 192.

The distal ends 216, 218 of the anode and cathode conductors 212, 214, respectively, have electrically conductive eyelets 226, 228 thereon. The eyelet 226 of the anode conductor 212 is positioned on and in direct electrical contact with the post 88 of the chuck assembly 70 and is secured thereon in an electrically conductive manner by a nut 107 and an electrically conductive washer 126 interposed between the base 60 and the eyelet 226. Since the eyelet 226 is in electrical contact with the spring-clip 58 through the washer 126, anode conductor 230 of the atrial temporary pervenous lead assembly secured to the chuck assembly 70 is provided with a first anode connection to the pacer 192 through the spring-clip 58 and a second anode connection through the conductor 212.

The eyelet 228 of the cathode conductor 214 is similarly positioned on and is in direct electrical contact with the post 88 of the chuck assembly 72 and secured thereon in an electrically conductive manner by a nut 107 with a nonconductive insulative washer 128 interposed between the base 60 and the eyelet 228. Since the eyelet 228 is in electrical contact with the post 88 of the chuck assembly 72, and insulated from the spring-clip 58 by the the washer 128, the conductor 232 of the atrial pacing lead assembly, which is secured to the chuck assembly 72 in an electrically conductive manner, is electrically connected to the eyelet 228 and to the cathode of the pacer 192 through the cathode conductor 214 and insulated from the spring-clip 58 thereby to provide a cathode connection for the atrial temporary pervenous lead assembly to the pacer 192 without shorting out the electrical system of the pacer 192.

Similarly, the plug assembly 210 includes an anode jumper conductor 234 and a cathode jumper conductor 236 having distal ends 238, 240, respectively, and proximal ends (not shown) electrically connected to the ventricular terminal lead plug 208. The proximal end of the anode conductor 234 is electrically connected to an anode ring 242 of the plug 208 and is in direct electrical contact with an anode sleeve 244 of the plug assembly receiving socket 202 in order to provide an anode connection for a ventricular temporary pervenous lead assembly (not shown) to the pacer 192.

The proximal end of the cathode conductor 236 is electrically connected to a cathode pin 246 which is in direct electrical contact with a cathode connector socket 248 of the plug assembly receiving socket 202 in order to provide a cathode connection for the ventricular temporary pervenous lead assembly to the pacer 192.

The distal ends 238, 240 of the conductors 212, 214, respectively, have electrically conductive eyelets 250, 252 thereon. The eyelets 250, 252 are positioned on and are in direct electrical contact with the threaded posts 88 of the fourth and third chuck assemblies 132, 130, respectively, and are secured thereon in an electrically conductive manner by a nut 107 with nonconductive, insulative washers 128 being interposed between the base 60 and the eyelets 250, 252. In this manner, an anode connection is provided between an anode conductor 254 of the ventricular pacing lead assembly (not shown) which is secured to the fourth chuck assembly 132 in an electrically conductive manner to the pacer 192. Similarly, a cathode connection is provided between a cathode conductor 256 of the ventricular pacing lead assembly which is secured to the third chuck assembly 130 in an electrically conductive manner to the pacer 192.

It is apparent that one of the advantages of the present invention is that an implantable cardiac pacer can be secured within the housing 12 of the adapter 10 in an electrically conductive manner by the spring-clip member 58 and externally worn by a patient so that a physician can try different pacers before choosing an appropriate cardiac pacer model to meet the pacing needs of the patient for implantation of an appropriate cardiac pacer into the patient before (and without) implanting any pacer in the patient.

Further, the adapter 10 can also be used to house other stimulating devices, such as a neurostimulator, prior to implantation of the neurostimulator or other stimulating device so that a physician is permitted to assess the efficacy of the neurostimulator before the neurostimulator is implanted.

From the foregoing description, it will be apparent that the adapter 10 and modifications 140 and 190 thereof, have a number of advantages, some of which have been described above and others of which are inherent in the invention. Also, it will be apparent that modifications can be made to the adapter without departing from the teachings of the present invention. Accordingly, the scope of the invention is only to be limited as necessitated by the accompanying claims.

We claim:

1. An adapter for converting a metal encapsulated implantable device, such as a cardiac pacer, to an externally worn device, said adapter comprising: a non-conductive housing; means for securing said device within said housing, said means for securing said device within said housing being in direct electrical contact with a metal housing of the device; and electrical interfacing means for securing a conductive lead assembly to said housing in an electrically conductive manner and means within said housing for electrically connecting said lead assembly to said device within said housing in an electrically conductive manner.

2. The adapter of claim 1 wherein said housing includes two side walls, an upper end wall and a lower end wall, said two side walls and said end walls defining an open area therebetween and said open area being further defined by a front panel and a back panel secured to said side walls and said end walls.

3. The adapter of claim 2 wherein said back panel is removavable.

4. The adapter of claim 1 wherein said non-conductive material is a polymeric material.

5. The adapter of claim 4 wherein said polymeric material is selected from the group comprising acrylonitrile butadiene styrene, polycarbonate, or other suitable polymers.

6. The adapter of claim 1 wherein said interfacing means for securing said lead assembly to said housing includes at least first and second electrically conductive chuck assemblies.

7. The adapter of claim 6 wherein said interfacing means for securing said lead assembly to said housing includes a third electrically conductive chuck assembly.

8. The adapter of claim 6 wherein said interfacing means for securing said lead assembly to said housing includes a fourth electrically conductive chuck assembly.

9. The adapter of claim 6 wherein each of said chuck assemblies include a conductive threaded post member which extends through a hole provided in said upper end wall, said post extending below said upper end wall and into said open area, and said chuck assemblies being upstanding from and perpendicular relative to said upper end wall and secured thereto by a threaded nut member, said threaded nut member being engagable with said threaded post member below said upper end wall.

10. The adapter of claim 6 wherein each of said chuck assemblies further includes a threaded cap member made of a nonconductive material, a conductive sleeve member having a conical configuration inserted in said cap member, a conductive threaded chuck seat member, and a plurality of conically configured conductive chuck members being freely positioned on said chuck seat member, said chuck seat member being connected to said post member and said cap member being threadably engeable with said seat member.

11. The adapter of claim 10 wherein each cap member includes an opening at its distal end adapted to receive a bared distal end of an electrical conductor, said chuck members being in an open position when said cap member is rotated in an upward or clockwise direction whereby an uninsulated end of a conductor is insertable into said opening and between said chuck members, and said chuck members conforming to said sleeve member of said cap member when said cap member is rotated in a downward or counterclockwise direction whereby said chuck members are urged relative to each other by said sleeve member so that the end of the conductor is secured between said chuck members in an electrically conductive manner and said chuck members with said seat member being in electrical contact with said threaded post member.

12. The adapter of claim 1 wherein said means for temporarily securing said pacer within said housing comprises a spring-clip member, said clip being U-shaped in configuration and comprising a base portion and two arm portions, said arm portions being biased inwardly at an angle relative to said base portion, and said base portion being provided with a plurality of holes having a diameter substantially larger than the diameter of said threaded posts and through which said threaded posts extend, said clip being secured to said upper end wall between said end wall and said threaded nut members and said arm portions extending downwardly into said open area.

13. The adapter of claim 12 wherein said spring-clip is rectangular in cross-section and is made of an electrically conductive material.

14. The adapter of claim 13 wherein said electrically conductive material is stainless steel.

15. The adapter of claim 12 wherein said distal ends of said arm portions turn inwardly and are parallel to said base portion and are urged relative to each other, a device such as a cardiac pacer being positionable between said distal ends and being in direct mechanical and electrical contact therewith such that the device can be secured between said distal ends in an electrically conductive manner.

16. The adapter of claim 6 wherein said interfacing means for electrically connecting said lead assembly to said pacer includes an anode jumper conductor and a cathode jumper conductor, said anode jumper conductor and said cathode jumper conductor having a distal end and a proximal end, each of said distal ends being connected to a terminal of said pacer, said proximal end of said anode conductor being in electrical contact with said base portion of said spring-clip and with said threaded post member of said first chuck assembly, and said proximal end of said cathode conductor being in direct electrical contact with said threaded post member of said second chuck assembly and being insulated from said base portion of said spring-clip member by an insulative washer interposed between said base member and said proximal end of said cathode jumper conductor.

17. The adapter of claim 7 wherein said means for electrically connecting said lead assembly to said pacer includes a jumper conductor having a proximal end and a distal end, said distal end being connected to a terminal of said pacer and said proximal end being in direct electrical contact with said threaded post member of said third chuck assembly and being insulated from said base portion of said spring-clip member by an insulative washer interposed between said base member and said proximal end of said conductor.

18. The adapter of claim 8 wherein said means for electrically connecting said lead assembly to said pacer includes two pairs of conductors each pair comprising an anode jumper conductor and a cathode jumper conductor, said anode jumper conductors and said cathode jumper conductors each having a distal end and a proximal end, each of said distal ends being connected to a terminal of said pacer, said proximal end of said jumper cathode conductors being in direct electrical contact with said threaded post member of said third chuck assembly and insulated from said base portion of said spring-clip member by an insulative washer interposed between said base member and said proximal end of said cathode jumper conductors, and said proximal end of at least one of said anode conductors being in electrical contact with said threaded post member of one of said chuck assemblies and in electrical contact with said base portion of said spring-clip member through a metallic conductive washer interposed between said base member and said proximal end of said cathode conductor.

19. The adapter of claim 2 wherein said front panel includes a transparent window made of a suitable polymeric material.

20. The adapter of claim 19 wherein said polymeric material is Mylar.

21. The adapter of claim 1 wherein said housing includes means for attaching said adapter to a body.

22. The adapter of claim 21 wherein said means for attaching said adapter to a body comprises two U-shaped wire bales which are rotatably secured between said upper and lower end walls and said removable rear wall, said wire bales being adapted to receive a fastening strap therethrough, which strap is adapted to be secured to the body.

* * * * *